United States Patent
Jacquemont et al.

(10) Patent No.: US 6,782,773 B1
(45) Date of Patent: Aug. 31, 2004

(54) SYSTEM FOR COUPLING A TOOTHED STARTER RING TO A SUPPORT CONNECTED TO THE OUTPUT SHAFT OF AN INTERNAL COMBUSTION ENGINE

(75) Inventors: Eric Jacquemont, Clisson (FR); Jean-Pierre Rocheteau, La Bruffiere (FR); Franck Douillard, La Bernardiere (FR)

(73) Assignee: S.A. Defontaine (FR)

( * ) Notice: Subject to any disclaimer, the term of this patent is extended or adjusted under 35 U.S.C. 154(b) by 158 days.

(21) Appl. No.: 09/671,624

(22) Filed: Sep. 28, 2000

(30) Foreign Application Priority Data

Sep. 30, 1999 (FR) .............................................. 99 12240
Dec. 21, 1999 (FR) .............................................. 99 16175

(51) Int. Cl.[7] ............................................... F16H 55/14
(52) U.S. Cl. ............................... 74/443; 74/461; 464/89
(58) Field of Search ............................... 464/89; 74/443, 74/446, 468, 574, 461, 462, 7 C

(56) References Cited

U.S. PATENT DOCUMENTS

| | | | | |
|---|---|---|---|---|
| 2,060,565 A | * | 11/1936 | Geyer | 464/89 X |
| 2,704,465 A | * | 3/1955 | Haller | 74/468 X |
| 2,885,870 A | * | 5/1959 | Jaklitsch | 464/89 |
| 3,200,659 A | * | 8/1965 | Angelini | 74/461 X |
| 3,262,435 A | * | 7/1966 | Cribbs | 74/461 X |
| 3,377,875 A | * | 4/1968 | Sand | 74/462 X |
| 3,854,418 A | | 12/1974 | Bertin | |
| 4,109,545 A | | 8/1978 | Hayasaka | 74/447 |
| 4,151,873 A | * | 5/1979 | Lewakowski | 74/443 X |
| 4,624,351 A | * | 11/1986 | Lutz et al. | 74/7 C X |
| 4,943,263 A | * | 7/1990 | Zyogahara et al. | 74/574 X |
| 5,251,725 A | * | 10/1993 | Barrett, Jr. | 74/468 X |
| 5,307,705 A | * | 5/1994 | Fenelon | 74/443 X |
| 5,911,788 A | | 6/1999 | Russ et al. | |

FOREIGN PATENT DOCUMENTS

| | | | | |
|---|---|---|---|---|
| DE | 31 32 503 | | 3/1983 | |
| FR | 788061 | | 10/1935 | |
| JP | 62-137443 | | 6/1987 | |
| JP | 1-120481 | | 5/1989 | |
| JP | 4-15352 | | 1/1992 | |
| JP | 4-63965 | | 2/1992 | |
| JP | 404034259 | * | 2/1992 | 464/468 |
| JP | 7-119600 | | 5/1995 | |
| JP | 9-133199 | | 5/1997 | |
| SE | 137058 | * | 6/1952 | 74/461 |

* cited by examiner

Primary Examiner—Greg Binda
(74) Attorney, Agent, or Firm—Bachman & LaPointe, P.C.

(57) ABSTRACT

In a system for coupling a toothed starter ring to a support connected to the output shaft of an internal combustion engine, a complementary substantially cylindrical peripheral surface of the ring is fixed over at least a part of its extent to a substantially cylindrical peripheral surface of the support in such a manner that the ring can deform slightly in the radial direction toward the shaft to reduce the maximum stresses exerted on the ring during a starting operation.

44 Claims, 4 Drawing Sheets

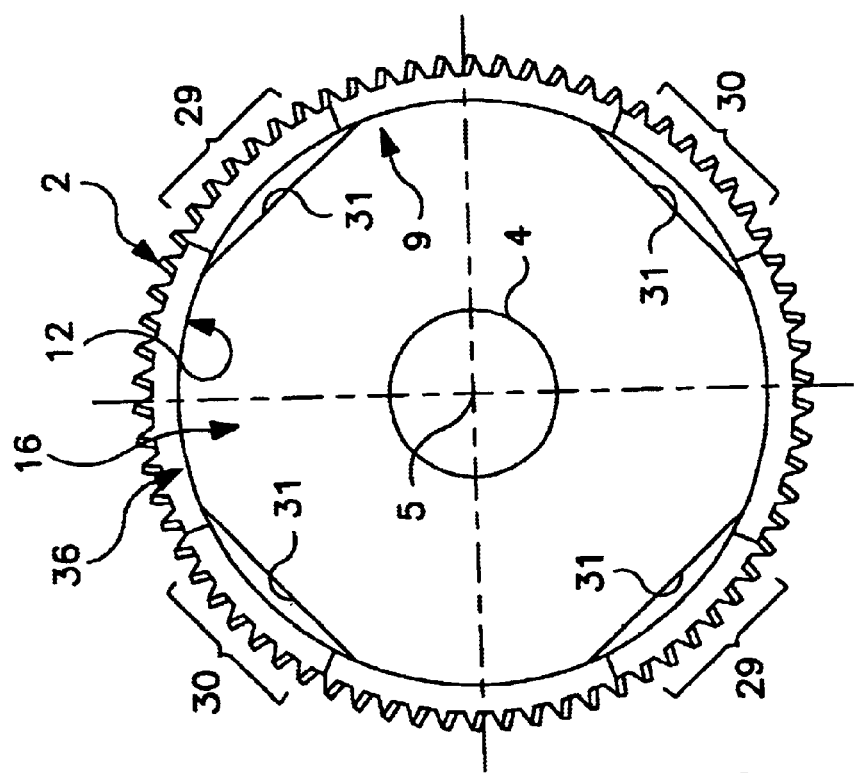
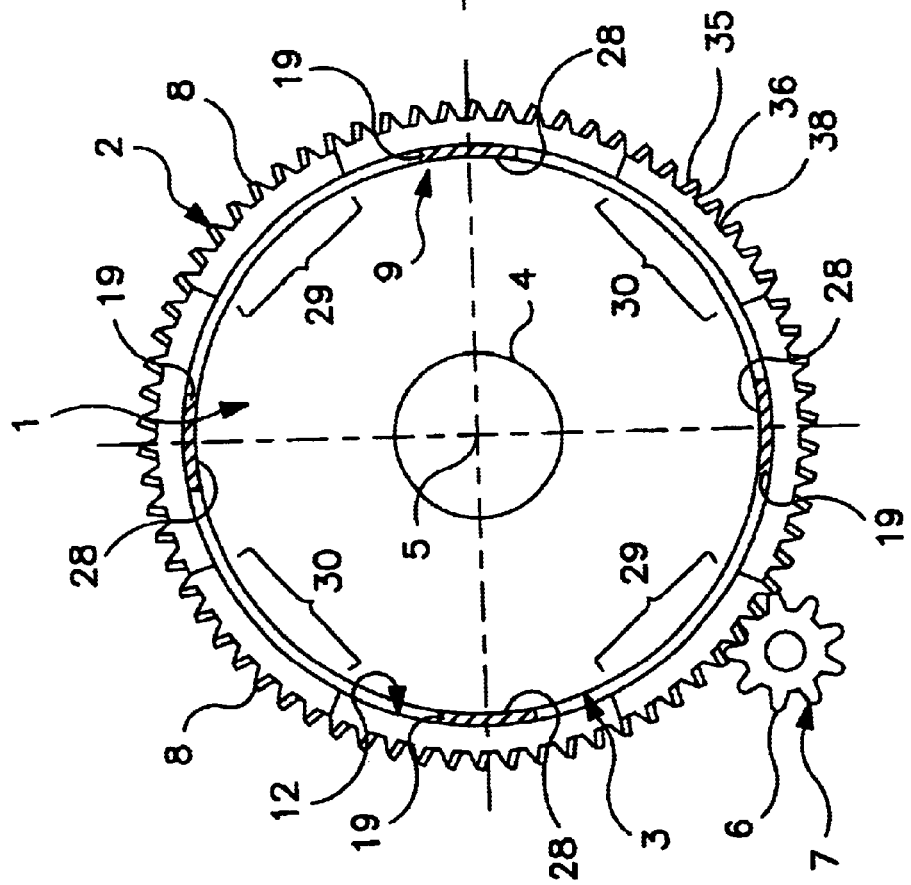
FIG. 8
FIG. 1

SYSTEM FOR COUPLING A TOOTHED STARTER RING TO A SUPPORT CONNECTED TO THE OUTPUT SHAFT OF AN INTERNAL COMBUSTION ENGINE

BACKGROUND OF THE INVENTION

1. Field of the Invention

The present invention relates to a system for coupling a toothed starter ring to a support connected to the output shaft of an internal combustion engine, in which system the support has a substantially cylindrical peripheral surface adapted to receive the ring and the ring has a substantially cylindrical inside peripheral surface complementary to the substantially cylindrical peripheral surface of the support and is adapted to cooperate with a rotor of a starter motor of the internal combustion engine.

2. Description of the Prior Art

The starter toothed ring is conventionally shrink-fitted, screwed or welded to its support, without leaving the ring any degree of freedom, in accordance with standard practice in the gearing art.

The support of the starter ring is generally the flywheel, or a member forming part of an assembly serving as a flywheel, of the internal combustion engine, and rotates with the latter.

A ring fixed to its support in this way is of satisfactory reliability. It is capable of withstanding and providing a number of engine starts of the order of 20 000 to 60 000, which is generally sufficient given the service life and average conditions of use of a vehicle.

However, starting an engine by the starter motor driving the starter ring and its support generates noise at an overall level greater than 90 decibels, and all parties involved, manufacturers and users, want a significant reduction in that level.

What is more, in the short- or medium-term, the fight against atmospheric pollution caused by the operation of internal combustion engines runs the risk of imposing the "stop/go," practice of stopping the engine of a vehicle when the vehicle is stopped, either at a red traffic light or because of a traffic jam.

In the case of vehicles used intensively in towns, this practice runs the risk of increasing the aforementioned number by a factor of at least four to six. In this case, a starter ring would have to withstand at least 200 000 engine starts, if riot 250 000 or 300 000, and perhaps many more.

FR-A-788 061 discloses a coupling system of the aforementioned type in which the ring is slidably mounted on an annular soundproofing material facing fixed to the cylindrical peripheral surface of the flywheel. Forces are transmitted between the ring and the flywheel either by a radial rubber ring glued to respective complementary radial faces of the ring and the flywheel or by rubber fingers engaged in notches on respective cylindrical peripheral surfaces of the flywheel and the ring.

A coupling system of the above kind, in which the whole of the ring can turn on its axis relative to the flywheel, cannot increase the service life of the aforementioned conventional system and does not have the required reliability.

The objects of the present invention are to remedy the drawbacks of conventional coupling systems known in the art and to propose a coupling system of the aforementioned type in which the ring is capable of withstanding a number of engine starts corresponding to the new figures indicated hereinabove, combined if possible with a significant reduction in noise level.

SUMMARY OF THE INVENTION

The invention provides a system for coupling a starter toothed ring to the peripheral part of a support connected to the output shaft of an internal combustion engine, the support including a substantially cylindrical peripheral surface adapted to receive the ring and the ring including a substantially cylindrical inside peripheral surface complementary to the peripheral surface of the support and adapted to cooperate with a rotor of a starter motor of the internal combustion engine, the axial faces of each tooth of the ring including, if necessary, a self-lubricating coating, wherein the complementary substantially cylindrical peripheral surface of the ring is fixed over at least part of its extent to the substantially cylindrical peripheral surface of the support in such a manner that the ring can deform slightly in the radial direction toward the shaft to reduce the maximum stresses exerted on the ring during a starting operation.

Some flexibility and some possibility of radial deformation are therefore imparted to the starter ring, which goes against gearing design rules.

In a manner that is entirely surprising, this damps the effect of impact on the teeth of the ring exposed to the pressure exerted by the teeth of the rotor of the starter motor on starting the engine.

The damping effect spectacularly increases the service life of the starter ring and that of the gear, which service life can correspond to a minimum of approximately 200 000 engine starting cycles.

The noise generated by the support and the starter ring when the rotor of the starter motor meshes with the ring is also reduced by an amount of the order of 5 to 7 decibels.

Other features and advantages of the present invention will become apparent in the course of the following detailed description, which is given with reference to the accompanying drawings, which are given by way of non-limiting example only.

BRIEF DESCRIPTION OF THE DRAWINGS

FIG. 1 is a diagrammatic elevation view of an internal combustion engine flywheel including a starter toothed ring fixed to a peripheral part of the flywheel by a coupling system constituting one embodiment of the invention.

FIG. 8 is a view similar to that of FIG. 1 of another embodiment of the present invention.

DETAILED DESCRIPTION OF THE PREFERRED EMBODIMENTS

Figure 2A:
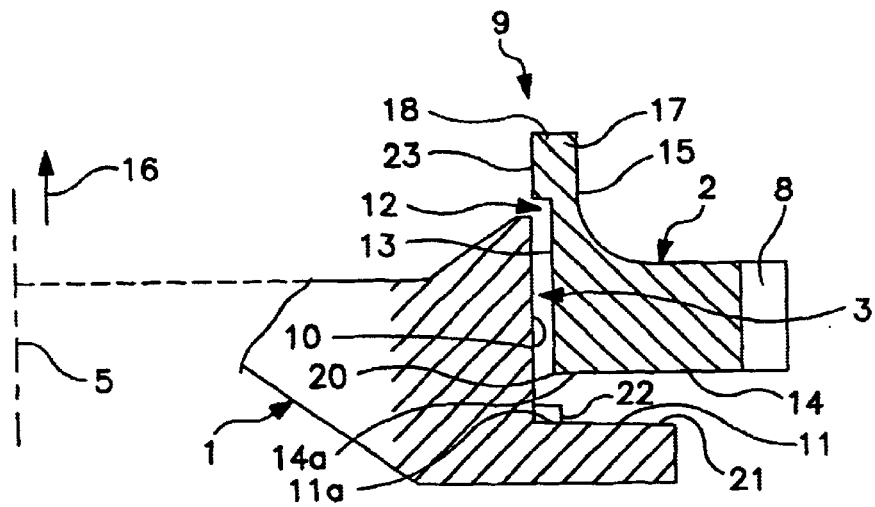
FIGS. 2A, 2B and 2C are diagrammatic views in axial section of a coupling system constituting one embodiment of the present invention, with the ring respectively shrink-fitted (FIGS. 2A and 2B) and welded (FIG. 2C) to the flywheel, the ring and the flywheel being offset axially in FIG. 2A to make the FIG. 2A clearer.

FIG. 1 shows diagrammatically an internal combustion engine flywheel 1 including a starter toothed ring 2 fixed to a peripheral part 3 of the flywheel 1.

The flywheel 1 is conventionally mounted on an output shaft 4 of an internal combustion engine (not shown). The shaft has an axis 5. To start an internal combustion engine (not shown), teeth 6 on a rotor 7 of a starter motor (not shown) mesh with teeth 8 on the ring 2 to drive rotation of the ring 2 and the flywheel 1.

A coupling system 9 according to the invention for coupling the starter toothed ring 2 to the peripheral part 3 of the support connected to the output shaft 4 of the internal combustion engine is described hereinafter in the simple and commonest situation in which the starter ring 2 is fixed directly to the peripheral part 3 of the flywheel 1.

Of course, the coupling system 9 according to the invention can be mounted and used identically on any support connected to the output shaft 4 of an internal combustion engine.

As shown in FIGS. 2A to 6, in the coupling system 9 according to the invention:

the peripheral part 3, 3a of the flywheel 1, 1a, 1b, 1c, 1d adapted to receive the ring 2, 2a, 2b, 2c has a shape in radial section in any radial plane corresponding substantially to an inside angle that is substantially a right angle, with a substantially cylindrical peripheral surface 10 for fixing the ring 2, 2a, 2b, 2c to the flywheel 1, 1a, 1b, 1c, 1d and a radial surface 11 of contact between the ring 2, 2a, 2b, 2c and the flywheel 1, 1a, 1b, 1c;

the inside peripheral part 12 of the ring 2, 2a, 2b, 2c adapted to be fixed to the flywheel 1, 1a, 1b, 1c, 1d has a shape in radial section complementary to the shape of the peripheral part 3, 3a of the flywheel 1, 1a, 1b, 1c, 1d, corresponding substantially to an outside angle that is substantially a right angle, with a substantially cylindrical inside peripheral surface 13, 13a, 13b, 13c, 13d complementary to the peripheral surface 10 and adapted to be fixed over at least a part of its extent to the peripheral surface 10 of the flywheel 1, 1a, 1b, 1c, and a radial surface 14 complementary to the radial surface 11 and adapted to be at least partly in contact with the radial surface 11 of the flywheel 1, 1a, 1b, 1c;

the complementary peripheral surface 13, 13a, 13b, 13c, 13d of the ring 2, 2a, 2b, 2c is fixed over at least a part of its extent to the peripheral surface 10 of the flywheel 1, 1a, 1b, 1c, at least in the region of the complementary peripheral surface 13, 13a, 13b, 13c, 13d at the greatest distance from the radial surface 14 of the ring 2, 2a, 2b, 2c, in such a manner that the ring 2, 2a, 2b, 2c can deform slightly in the radial direction toward the shaft 4 when starting the engine and the complementary radial surface 14 of the ring 2, 2a, 2b, 2c can slide slightly along the radial surface 11 of the flywheel 1, 1a, 1b, 1c.

Figure 2B:
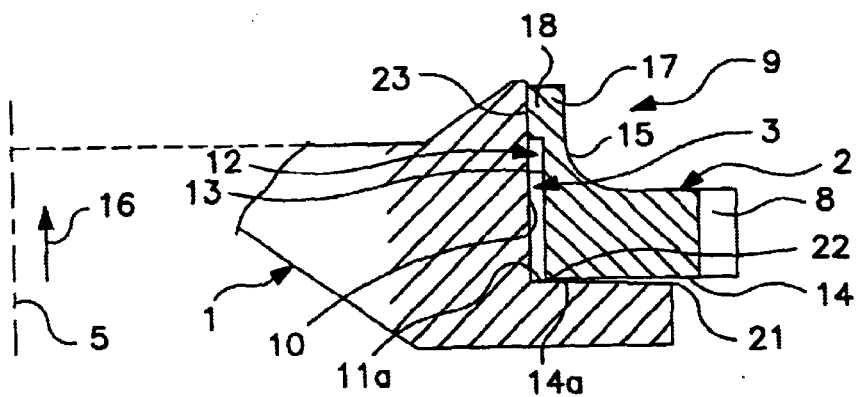
Figure 2C:
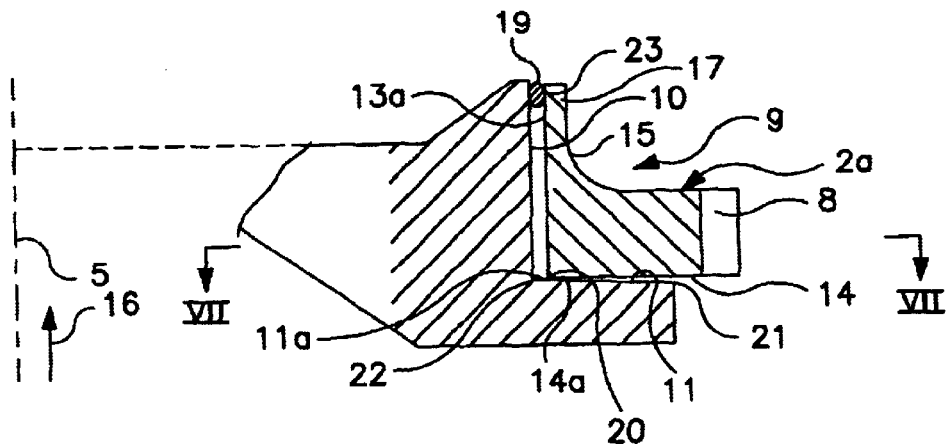

In the embodiment shown in FIGS. 2A, 2B and 2C, the ring 2, 2a has an annular part 15 extending axially beyond the teeth 8 in the axial direction 16 away from the complementary radial surface 14 and toward the rotor 7 and the ring 2, 2a is fixed to the flywheel 1 at the axial end 17 of the annular part 15.

In the embodiment shown in FIGS. 2A and 2B the axial end 17 includes an inner flange 18 projecting radially inward toward the axis 5 and delimited internally by a cylindrical internal peripheral surface 23 adapted to be in contact with the peripheral surface 10 of the flywheel 1 and to be fixed thereto.

This embodiment is preferably shrink-fitted to the flywheel 1, as shown in FIG. 2B.

In the embodiment shown in FIG. 2C the peripheral surface 23 of the axial end 17 of the annular part 15 is fixed to the peripheral surface 10 of the flywheel 1 by a weld 19.

Outside the regions in which the ring 2, 2a is fixed to the flywheel 1, the remainder of the complementary substantially cylindrical surface 13, 13a is shaped so that it is radially spaced from the cylindrical surface 10 of the flywheel 1 to impart the required radial flexibility to the ring 2, 2a.

In the embodiment shown in FIGS. 2A to 2C the region 14a of the complementary radial surface 14 of the ring 2, 2a adapted to be in contact with the radial surface 11 of the flywheel 1 extends radially a short distance from the circular edge 20 constituting the corresponding corner of the axial section of the ring as shown in the figures, i.e. the bottom right-hand corner.

Correspondingly, the region 11a of the radial surface 11 of the flywheel 1 adapted to be in contact with the region 14a of the ring extends radially a short distance from the peripheral surface 10 so that it comes into sliding contact with the region 14a of the complementary radial surface 14 of the ring 2, 2a which has a small radial dimension. The radial surface 11 is therefore extended by a widely flared conical surface 21 which has the same axis 5. This facilitates fitting the ring 2, 2a to the flywheel 1.

A thin coating 22 of a material facilitating sliding contact between the radial surface 11 and the complementary radial surface 14, for example an elastomer or a plastomer, fixed to the radial surface 11 of the flywheel 1 is shown diagrammatically in FIG. 2A, in which its axial dimension is greatly exaggerated to make the figure clearer.

Figure 3A:
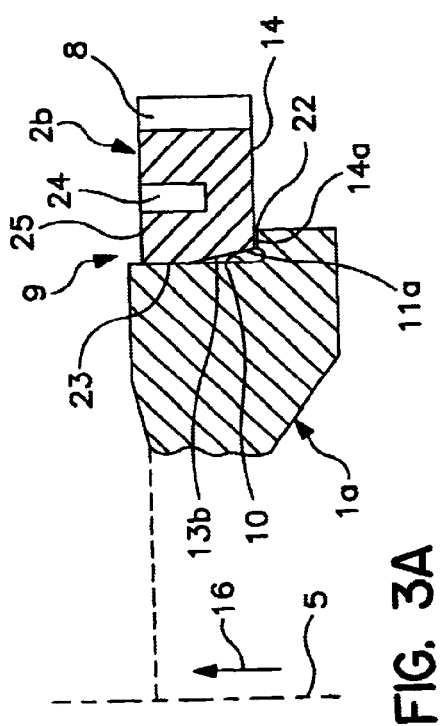
FIGS. 3A and 3B are views respectively similar to those of FIGS. 2A and 2C but corresponding to a different embodiment of the present invention.
Figure 3B:
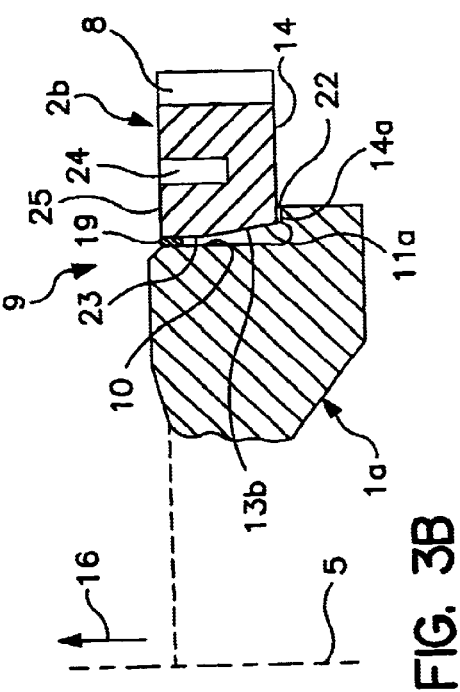

In the embodiment shown in FIGS. 3A and 3B, the complementary inside peripheral surface 13b of the ring 2, 2b has an axial dimension that preferably corresponds substantially to that of the teeth 8. The ring 2, 2b is fixed, for example welded or shrink-fitted, to the flywheel 1a in the region 23 of the complementary peripheral surface 13b at the greatest distance from the complementary radial surface 14. The ring 2b further includes an annular groove 24 starting from the surface 25 delimiting the ring 2b in the axial direction 16 toward the rotor 7, away from the complementary radial surface 14, and extending axially toward the complementary radial surface 14 over a part of the axial dimension of the ring 2b.

The region 23 shown in FIG. 3A has an axial dimension sufficient to enable the ring 2b to be shrink-fitted to the surface 10 of the flywheel 1a.

In the FIG. 3B example, the ring 2b is fixed to the flywheel 1a by a weld 19 at the axial end of the region 23 opposite the complementary radial surface 14.

In the embodiment shown in FIGS. 3A and 3B, the contact region 11a of the radial surface 11 of the flywheel 1a is radially outside the peripheral surface 10, and extends a short distance in the radial direction. It carries a thin elastomer or plastomer coating 22 enabling sliding contact with the region 14a of the complementary radial surface 14 of the ring 2b.

In this embodiment the flywheel 1a does not extend radially outward beyond the region 11a, and the ring is therefore entirely free to deform when starting the engine.

Figure 4:
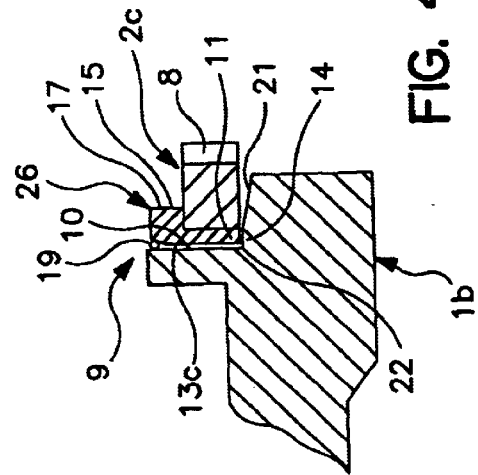
FIG. 4 is a diagrammatic view similar to that of FIG. 2C of another embodiment of the present invention.

In the embodiment shown diagrammatically in FIG. 4 the flywheel includes an intermediate annular metal member 26 to which the ring 2c is fixed in any conventional way, for example screwed, shrink-fitted or welded.

The intermediate annular member 26 includes the complementary inside peripheral surface 13c and the complementary radial surface 14. The intermediate annular member 26 is fixed to the flywheel 1b at its axial end at a distance from the complementary radial surface 14 as if the intermediate member 26 were an integral part of the ring 2c. It is fixed to the flywheel 1b in any manner known in the art.

In the embodiment shown, the intermediate member 26 has a greater length in the axial direction than the ring 2c. It is fixed to the flywheel 1b by a weld 19 at its axial end 17 at a distance from the complementary radial surface 14.

Thus as seen in FIGS. 3A, 3B and 4, the substantially cylindrical peripheral surfaces 10, 13 of the ring 2b, 2c and the support 1a, 1b, respectively, are connected to each other by a metal-to-metal fixation, i.e., a shrink fit, a weld or an intermediate annular metal member, respectively.

Figure 5:
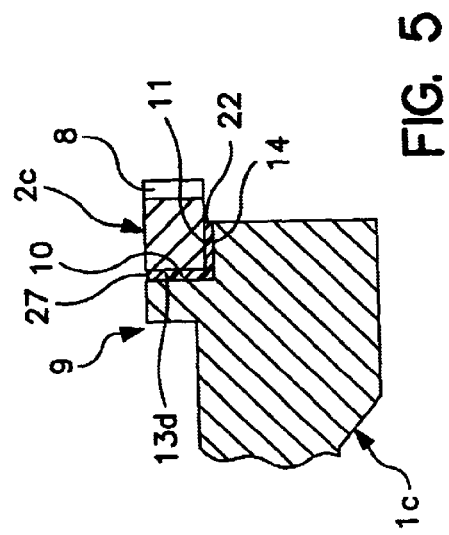
FIG. 5 is a view similar to that of FIG. 4 showing a further embodiment of the present invention.

In the embodiment shown diagrammatically in FIG. 5 the flywheel 1c includes an annular ring 27 of a deformable material, for example an elastomer or plastomer, extending axially along the complementary peripheral surface 13d of the ring 2c. The ring 27 is glued or stuck by any means known in the art to the peripheral surface 10 of the flywheel 1c on one side and to the peripheral surface 13d of the ring 2c on the other side.

The annular ring 27 necessarily has sufficient thickness to impart to the ring 2c sufficient freedom of deformation relative to the flywheel 1c to obtain the effects sought by the present invention.

Furthermore, an elastomer or plastomer coating 22 is fixed to the radial surface 11, for example, to enable sliding contact with the complementary radial surface 14 of the ring 2c.

Figure 6:
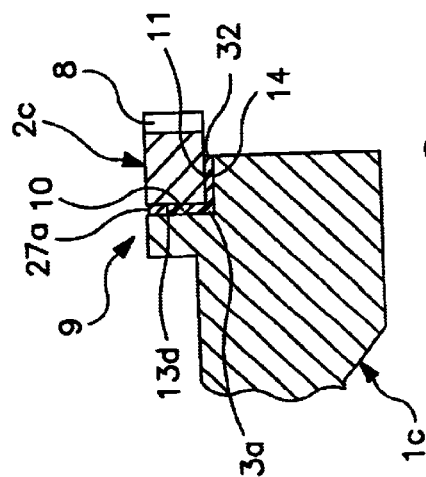
FIG. 6 is a view similar to that of FIG. 5 showing a variant of the embodiment shown in FIG. 5.

In the embodiment shown in FIG. 6, the annular ring 27a has an L-shaped radial section and includes a radial wall 32 stuck to the radial surface 11 of the support 1c on one side and to the complementary radial surface 14 of the ring 2c on the other side.

The ring 27a can therefore be easily made by pressurized injection of the elastomer into the L-shaped space between the support 1c and the ring 2c.

Figure 7:
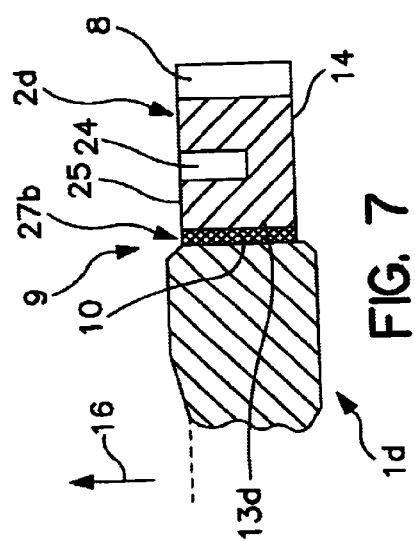
FIG. 7 is a view similar to that of FIG. 5 showing another variant of the embodiment shown in FIG. 5.

In the embodiment shown in FIG. 7 the peripheral part 3a of the flywheel 1c comprises only the cylindrical surface 10, with no radial wall.

The conventional radial wall 11 serves both to locate the ring 2c accurately on the flywheel 1c during fabrication of the flywheel and to absorb some of the axial force transmitted by the rotor 7 of the starter motor to the ring 2c when starting the engine. This is known in the art.

In the absence of the conventional wall 11, the ring 2c must be fixed to the support by means adapted to absorb all of the axial force.

In the embodiment shown in FIG. 7 a visco-elastic material annular ring 27b is stuck to the peripheral surface 10 of the flywheel 1d on one side and to the peripheral surface 13d of the ring 2d on the other side.

In this embodiment, the ring 2d includes the annular groove 24 described above.

The annular ring can also be made of metal in the embodiment described below with reference to FIG. 8.

The ring 2 is preferably fixed to the flywheel 1 only in peripheral sectors 28 (FIG. 1) regularly distributed about the axis 5 of the flywheel 1, leaving free the diametrally opposite sectors 29 corresponding to the compression stroke of an internal combustion engine equipped with the flywheel concerned and/or the diametrally opposite sectors 30 corresponding to the expansion stroke of the engine, the sectors 29 and 30 being readily identified relative to the top dead center position conventionally marked on every flywheel. This applies especially in the case of welding (see FIG. 1) or shrink-fitting (see FIG. 6).

This makes it possible to impart additional flexibility to the ring in the compression sectors 29 and expansion sectors 30, increasing the damping of the impact effect and of the pressure peak to which the teeth 8 of the ring 2 are subjected in the compression sectors 29 and expansion sectors 30.

The FIG. 1 embodiment relates to a four-cylinder engine and this figure shows four fixing sectors 28 at the ends of two perpendicular axes, each compression or expansion sector 29, 30 being situated between two adjacent fixing sectors 28. A different number of sectors 28 could be used, for example six sectors 28 for a three-cylinder engine or a V6 engine.

In the embodiment shown in FIG. 8 the peripheral surface of the flywheel 1d has a recess 31 level with each of the two sectors 29 corresponding to the two compression areas and/or with each of the two sectors 30 corresponding to the two expansion areas.

The recesses 31 are formed by any manner known in the art, and take the form of flats, for example which are formed during molding or by milling, or grooves of any peripheral shape.

Accordingly, the ring 2, which is not locked to the flywheel at the level of the recesses 31, has an additional radial flexibility which reduces the stresses and the wear to which the ring is usually exposed in the sectors 29 and 30 corresponding to the compression and expansion areas.

Thus various systems for coupling a ring 2, 2a, 2b, 2c, 2d to a flywheel 1, 1a, 1b, 1c, 1d have been described. Some of these coupling systems include fixing means as far as possible from the complementary radial surface 14 of the ring, imparting to the ring 2, 2a, 2b, 2c, 2d a radial flexibility relative to the flywheel 1, 1a, 1b, 1c, 1d which is facilitated by sliding contacts over a generally small radial distance between the complementary radial surface 14 of the ring 2, 2a, 2b, 2c, 2d and the radial surface 11 of the flywheel 1, 1a, 1b, 1c, 1d.

All the embodiments described impart flexibility to the ring in the radial direction toward the axis 5, without excluding flexibility in other directions.

Of course, for each coupling system described, the shape of the radial section of the ring is designed to enable the ring to withstand the stresses caused by the fixing mode adopted. In any event, those stresses are exerted in a non-hardened stress area because the hardened area Which includes the teeth extends inward only approximately 1 millimeter below the teeth.

In all of the foregoing description, the coupling system according to the present invention connects the ring to the flywheel or its support, that coupling concerning at least partly the outside peripheral surface 10 of the flywheel 1, 1a, 1b, 1c, 1d and the inside peripheral surface 13, 13a, 13b, 13c, 13d of the ring 2, 2a, 2b, 2c, 2d.

The examples described above show that the term "partly" must be interpreted geometrically and means that the coupling surface extends along a part or over a part at least of the peripheral surfaces 10 and 13, 13a, 13b, 13c, 13d, in the peripheral direction as well as in the axial direction.

The coupling systems and the systems for damping the mechanical stresses to which the teeth 8 of the toothed ring 2, 2a, 2b, 2c, 2d are subjected described above effectively achieve the stated objective of 200 000 to 300 000 engine starts, and where necessary many more.

We have continued our research and our efforts to make the toothed ring stronger whilst reducing the noise level generated by an engine start.

We have therefore combined one of the above coupling and damping systems with lubrication of the teeth of the toothed ring by a film of oil or grease deposited in any manner known in the art, for example by sprinkling, by spraying a pressurized jet or by simple contact of the teeth with a contact member coated with oil or grease of any appropriate quality known in the art. Systematic tests of a combination of the above kind of a coupling system and a lubrication system have enabled a toothed ring to achieve more than 800 000 engine starts without the ring or any tooth breaking.

Figure 9:
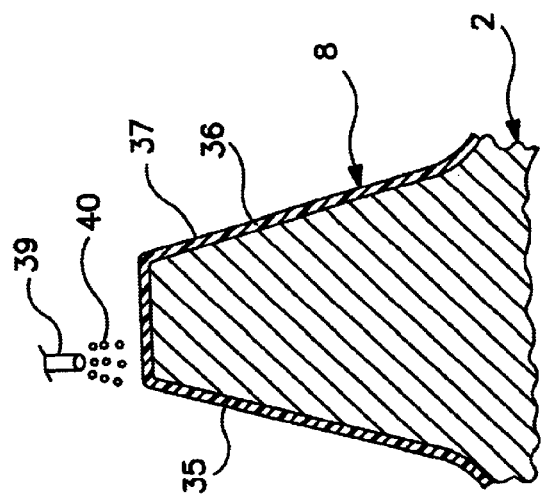
FIG. 9 is a highly enlarged diagrammatic view in cross section taken along the line VII—VII in FIG. 2C, for example, of a tooth of a toothed ring fixed by a coupling system constituting an embodiment of the present invention.

Alternatively, and as shown diagrammatically in FIG. 9, we have applied a self-lubricating coating 37 at least to the two axial faces 35, 36 of each tooth 8. The thickness of the coating is greatly exaggerated in the figure to make it clearer.

The coating 37 can obviously also coat the surface 38 between two adjacent teeth 8 (see FIG. 1) or be limited to the faces 35 and 36.

A coating of the above kind is known in the art. It can, for example, be a sliding varnish of the SDA® type sold by TECHNIQUES SURFACES® and applying solid lubricants to the surface of the treated parts, such as molybdenum bisulfide, in a thermosetting matrix based on epoxy, phenolic, silicone, etc. resins, alone or in a mixture. A coating of the above kind can be formed by spraying, for example, or by dipping or by centrifugal means on surfaces that have received an appropriate surface treatment beforehand.

A coating of the above kind can instead be the result of a surface treatment known as SULF BT® from TECHNIQUES SURFACES TS®, carried out by anodic electrolysis in a bath of molten salts based on alkaline thiocyanates. The treatment forms a microlayer of iron sulfide totally interleaved with the base metal on the treated surfaces and having a thickness from approximately 7 microns to approximately 8 microns.

A self-lubricating coating of the above kind can obviously be associated with lubrication with an appropriate oil or grease applied by any appropriate lubrication means known in the art, as symbolized at 39 in FIG. 9, for example a nozzle for spraying droplets of oil 40.

Of course, the present invention is not limited to the embodiments that have just been described, to which many changes and modifications can be made without departing from the scope of the invention.

For example, other means known in the art can be used to facilitate sliding contact between the regions 11a and 14a instead of the coating 22. The two regions could also be polished, or a metal or plastics anti-friction material deposited on them. Such means could also be dispensed with.

Instead of having a peripheral surface of the support and a peripheral surface of the ring separated over a part of the surface, there could be a cylindrical peripheral surface on the ring and a peripheral surface on the support conformed to be radially separated from the surface over a part of its extent.

Finally, the various embodiments described hereinabove can be combined with each other in any manner.

What is claimed is:

1. An internal combustion engine flywheel comprising:
a support connected to an output shaft of an internal combustion engine and a starter toothed ring adapted to cooperate with a rotor of a starter motor of said internal combustion engine,
said support having a peripheral part which receives said ring and includes a substantially cylindrical peripheral surface for fixing said ring to said support, and
said ring having an inside peripheral part which is fixed to said support and includes a substantially cylindrical inside peripheral surface complementary to said peripheral surface of said support, wherein
said complementary substantially cylindrical peripheral surface of said ring is fixed over at least part of its extent to said substantially cylindrical peripheral surface of said support in such a manner that said ring is deformable in the radial direction toward said shaft to reduce the maximum stresses exerted on said ring during a starting operation, and
said substantially cylindrical peripheral surfaces are connected to each other by a metal-to-metal fixation.

2. The internal combustion engine flywheel claimed in claim 1, wherein:
said peripheral part of said support with said substantially cylindrical peripheral surface and a radial surface of contact between said ring and said support has a shape so as to form in radial section an inside angle that is substantially a right angle,
said inside peripheral part of said ring with said complementary substantially cylindrical inside peripheral surface and a complementary radial surface in contact over at least a part of its extent with said radial surface of said support has a complementary shape so as to form in radial section an outside angle that is substantially a right angle, and
said complementary peripheral surface of said ring is fixed over at least a part of its extent to said peripheral surface of said support in such a manner that said complementary radial surface of said ring is slidable along said radial surface of said support.

3. The internal combustion engine flywheel claimed in claim 2, wherein said ring includes an annular groove extending axially inwardly from an external radial surface delimiting said ring opposite said complementary radial surface.

4. The internal combustion engine flywheel claimed in claim 1, wherein said ring includes an annular groove extending axially inwardly from an external radial surface delimiting said ring toward said rotor.

5. The internal combustion engine flywheel claimed in claim 1, wherein said complementary peripheral surface is welded to said peripheral surface of said support.

6. The internal combustion engine flywheel claimed in claim 1, wherein said complementary peripheral surface is shrink-fitted to said peripheral surface of said support.

7. An internal combustion engine flywheel comprising:
a support connected to an output shaft of an internal combustion engine and a starter toothed ring adapted to cooperate with a rotor of a starter motor of said internal combustion engine,
said support having a peripheral part which receives said ring and includes a substantially cylindrical peripheral surface for fixing said ring to said support, and
said ring having an inside peripheral part which is fixed to said support and includes a substantially cylindrical inside peripheral surface complementary to said peripheral surface of said support,
wherein said complementary substantially cylindrical peripheral surface of said ring is fixed over at least part of its extent to said substantially cylindrical peripheral surface of said support, and said ring includes an annular groove extending axially inwardly from an external radial surface delimiting said ring toward said rotor in such a manner that said ring is deformable in the radial direction toward said shaft to reduce the maximum stresses exerted on said ring during a starting operation.

8. The internal combustion engine flywheel claimed in claim 7, wherein:

said peripheral part of said support with said substantially cylindrical peripheral surface and a radial surface of contact between said ring and said support has a shape so as to form in radial section and inside angle that is substantially a right angle, said inside peripheral part of said ring with said complementary substantially cylindrical inside peripheral surface and a complementary radial surface in contact over at least a part of its extent with said radial surface of said support has a complementary shape so as to form in radial section an outside angle that is substantially a right angle, said complementary peripheral surface of said ring is fixed over at least a part of its extent to said peripheral surface of said support in such a manner that said complementary radial surface of said ring is slidable along said radial surface of said support, and said external radial surface from which said annular groove extends is opposite said complementary radial surface.

9. The internal combustion engine flywheel claimed in any one of claims 1 and 7, wherein said ring is fixed to said support only in peripheral fixing sectors regularly distributed around the axis of said support, leaving free at least one of:

diametrically opposed sectors corresponding to compression areas; and diametrically opposed sectors corresponding to expansion areas.

10. The internal combustion engine flywheel claim in any one of claims 1 or 7, wherein said peripheral surface of said support has a recess in at least one of:

the area of each of diametrically opposed sectors corresponding to compression areas; and the area of each diametrically opposed sectors corresponding to expansion areas.

11. An internal combustion engine flywheel comprising:

a support connected to an output shaft of an internal combustion engine and a starter toothed ring adapted to cooperate with a rotor of a starter motor of said internal combustion engine, said support having a peripheral part which receives said ring and includes a substantially cylindrical peripheral surface for fixing said ring to said support, and said ring having an inside peripheral part which is fixed to said support and includes a substantially cylindrical inside peripheral surface complementary to said peripheral surface of said support, wherein said peripheral surface of said support has a recess in the area of each of at least one of:

diametrically opposed sectors corresponding to compression areas, and diametrically opposed sectors corresponding to expansion areas; and said complementary substantially cylindrical peripheral surface of said ring is fixed to said substantially cylindrical peripheral surface of said support only between said recesses in such a manner that said ring is deformable in the radial direction toward said shaft to reduce the maximum stresses exerted on said ring during a starting operation.

12. The internal combustion engine flywheel claimed in claim 11, wherein:

said peripheral part of said support with said substantially cylindrical peripheral surface and a radial surface of contact between said ring and said support has a shape so as to form in radial section an inside angle that is substantially a right angle, said inside peripheral part of said ring with said complementary substantially cylindrical inside peripheral surface and a complementary radial surface in contact over at least a part of its extent with said radial surface of said support has a complementary shape so as to form in radial section an outside angle that is substantially a right angle, and said complementary peripheral surface of said ring is fixed over at least a part of its extent to said peripheral surface of said support in such a manner that said complementary radial surface of said ring is slidable along said radial surface of said support.

13. The internal combustion engine flywheel claimed in any one of claims 2, 8 and 12, wherein said ring is fixed to said peripheral surface of said support in a region of said complementary peripheral surface at a distance from said complementary radial surface, and the remainder of said complementary peripheral surface is shaped in such manner that it is radially separated from said peripheral surface of said support.

14. The internal combustion engine flywheel claimed in claim 13, wherein said ring has a plurality of teeth and an annular part extending axially beyond said teeth in the axial direction away from said complementary radial surface, said annular part has an axial end opposite to said complementary radial surface, and said complementary inside peripheral surface of said ring at said axial end constitutes said region fixed to said peripheral part of said support.

15. The internal combustion engine flywheel claimed in claim 13, wherein said ring is fixed to an intermediate member which includes said region of said complementary peripheral surface and said complementary radial surface.

16. The internal combustion engine flywheel claimed in any one of claims 2, 8 and 12, wherein a material favoring sliding of said complementary radial surface of said ring on said radial surface of said support is disposed between said two radial surfaces.

17. The internal combustion engine flywheel claimed in claim 16, wherein said material favoring said sliding is a coating fixed to said radial surface of said support.

18. The internal combustion engine flywheel claimed in claim 16, wherein said material favoring said sliding is an elastomer.

19. The internal combustion engine flywheel claimed in claim 16, wherein said material favoring said sliding is a plastomer.

20. The internal combustion engine flywheel claimed in claim 12, which includes an annular deformable ring having in radial section an L-shaped section, stuck to said peripheral surface and to said radial surface of said support on one side, and to said complementary peripheral surface and to said complementary radial surface of said ring on the other side.

21. The internal combustion engine flywheel claimed in claim 20, wherein said annular deformable ring is an elastomer.

22. The internal combustion engine flywheel claimed in claim 20, wherein said annular deformable ring is a plastomer.

23. The internal combustion engine flywheel claimed in any one of claims 2, 8 and 12 wherein said ring is fixed to an intermediate member which includes said complementary peripheral surface and said complementary radial surface.

24. The internal combustion engine flywheel claimed in any one of claims 1, 7 and 11, wherein said ring is fixed to an intermediate member which includes said complementary inside peripheral surface.

25. The internal combustion engine flywheel claimed in any one of claims 7 and 11 which includes an annular deformable ring stuck to said peripheral surface of said support on one side and to said complementary peripheral surface of said ring on the other side.

26. The internal combustion engine flywheel claimed in claim 25, wherein said annular deformable ring is an elastomer.

27. The internal combustion engine flywheel claimed in claim 25, wherein said annular deformable ring is a plastomer.

28. The internal combustion engine flywheel claimed in any one of claims 1, 7 and 11, wherein said flywheel is associated with means for lubricating an external radial toothed surface of said ring.

29. The internal combustion engine flywheel claimed in any one of claims 1, 7 and 11, wherein the external radial toothed surface of said ring includes a self-lubricating coating.

30. An internal combustion engine flywheel comprising:
a support connected to an output shaft of an internal combustion engine and a starter toothed ring adapted to cooperate with a rotor of a starter motor of said internal combustion engine,
said support having a peripheral part which receives said ring and includes a substantially cylindrical peripheral surface for fixing said ring to said support, and
said ring having an inside peripheral part which is fixed to said support and includes a substantially cylindrical inside peripheral surface complementary to said peripheral surface of said support,
wherein said complementary substantially cylindrical peripheral surface of said ring is fixed over at least part of its extent to said substantially cylindrical peripheral surface of said support in such a manner that said ring is deformable in the radial direction toward said shaft to reduce the maximum stresses exerted on said ring during a starting operation,
said peripheral part of said support with said substantially cylindrical peripheral surface and a radial surface of contact between said ring and said support has a shape so as to form in radial section an inside angle that is substantially a right angle,
said inside peripheral part of said ring with said complementary substantially cylindrical inside peripheral surface and a complementary radial surface in contact over at least a part of its extent with said radial surface of said support has a complementary shape so as to form in radial section an outside angle that is substantially a right angle, and
said complementary peripheral surface of said ring is fixed over at least a part of its extent to said peripheral surface of said support in such a manner that said complementary radial surface of said ring is slidable along said radial surface of said support.

31. The internal combustion engine flywheel according to claim 30, wherein said ring is fixed to said peripheral surface of said support in a region of said complementary peripheral surface at a distance from said complementary radial surface, and the remainder of said complementary peripheral surface is shaped in such manner that it is radially separated from said peripheral surface of said support.

32. The internal combustion engine flywheel claimed in claim 31, wherein said ring has an annular part extending axially beyond said teeth in the axial direction away from said complementary radial surface, said annular part has an axial end opposite to said complementary radial surface, and said complementary inside peripheral surface of said ring at said axial end constitutes said region fixed to said peripheral part of said support.

33. The internal combustion engine flywheel of claim 30, wherein a material favoring sliding of said complementary radial surface of said ring on said radial surface of said support is disposed between said two radial surfaces.

34. An internal combustion engine flywheel comprising:
a support connected to an output shaft of an internal combustion engine and a starter toothed ring adapted to cooperate with a rotor of a starter motor of said internal combustion engine,
said support having a peripheral part which received said ring and includes a substantially cylindrical peripheral surface for fixing said ring to said support, and
said ring having an inside peripheral part which is fixed to said support and includes a substantially cylindrical inside peripheral surface complementary to said peripheral surface of said support, wherein
said complementary substantially cylindrical peripheral surface of said ring is fixed over at least part of its extent to said substantially cylindrical peripheral surface of said support in such a manner that said ring is deformable in the radial direction toward said shaft to reduce the maximum stresses exerted on said ring during a starting operation, and
said ring is fixed to said support only in peripheral fixing sectors regularly distributed around the axis of said support, leaving free diametrically opposed sectors corresponding to compression areas and/or diametrically opposed sectors corresponding to expansion areas.

35. An internal combustion engine flywheel comprising:
a support connected to an output shaft of an internal combustion engine and a starter toothed ring adapted to cooperate with a rotor of a starter motor of said internal combustion engine,
said support having a peripheral part which receives said ring and includes a substantially cylindrical peripheral surface for fixing said ring to said support, and
said ring having an inside peripheral part which is fixed to said support and includes a substantially cylindrical inside peripheral surface complementary to said peripheral surface of said support, wherein
said complementary substantially cylindrical peripheral surface of said ring is fixed over at least part of its extent to said substantially cylindrical peripheral surface of said support in such a manner that said ring is deformable in the radial direction toward said shaft to reduce the maximum stresses exerted on said ring during a starting operation, and
said peripheral surface of said support has a recess in at least one of:
the area of each diametrically opposed sectors corresponding to compression areas, and the area of each diametrically opposed sectors corresponding to expansion areas.

36. A flywheel assembly for an internal combustion engine comprising:
   a metallic flywheel having a substantially cylindrical outside peripheral surface; and
   a metallic starter toothed ring having a substantially cylindrical inside peripheral surface,
   wherein at least a first portion of said outside peripheral surface of said flywheel engages said inside peripheral surface of said toothed ring by metal-to-metal fixation, and
   a second portion of said outside peripheral surface of said flywheel is spaced from said inside peripheral surface of said toothed ring to create a gap therebetween, said gap permitting radial deformation of said toothed ring during a starting operation.

37. The flywheel assembly of claim 36, wherein said metal-to-metal fixation comprises at least one of a shrink fit, a weld, and an intermediate annular metal member.

38. The flywheel assembly of claim 36, wherein said second portion of said outside peripheral surface of said flywheel is slidably associated with said inside peripheral surface of said toothed ring.

39. The flywheel assembly of claim 36, wherein said toothed ring further comprises an annular groove and a plurality of teeth, said annular groove being disposed between said inside peripheral surface and said teeth.

40. The flywheel assembly of claim 36, wherein said outside peripheral surface of said flywheel comprises at least one substantially cylindrical portion and at least one recessed portion, and said metal-to-metal fixation is disposed only along said at least one substantially cylindrical portion.

41. The flywheel assembly of claim 40, wherein the at least one recessed portion comprises at least one of a recess, a flat, and a groove.

42. The flywheel assembly of claim 40, comprising at least one pair of opposed, substantially cylindrical portions, and at least one pair of opposed, recessed portions.

43. The flywheel assembly of claim 40, wherein a number of separate portions of said outside peripheral surface of said flywheel that engage said inside peripheral surface of said toothed ring by metal-to-metal fixation corresponds to a number of cylinders of an internal combustion engine in which the flywheel assembly is installed.

44. The flywheel assembly of claim 40, wherein a number of recessed portions of said outside peripheral surface of said flywheel corresponds to a number of cylinders of an internal combustion engine in which the flywheel assembly is installed.

* * * * *